US009396884B2

(12) United States Patent
Galiano et al.

(10) Patent No.: US 9,396,884 B2
(45) Date of Patent: Jul. 19, 2016

(54) IONIC LIQUIDS THAT CAN BE USED AS PART OF THE ELECTROLYTE COMPOSITION FOR ENERGY STORAGE DEVICES

(75) Inventors: Herve Galiano, La Ville aux Dames (FR); Mérièm Anouti, St Avertin (FR); Daniel Lemordant, Vouvray (FR); Laure Timperman, St Avertin (FR)

(73) Assignees: Commissariat à l'énergie atomique et aux énergies alternatives, Paris (FR); Université François Rabelais, Tours (FR)

( * ) Notice: Subject to any disclaimer, the term of this patent is extended or adjusted under 35 U.S.C. 154(b) by 109 days.

(21) Appl. No.: 14/237,091

(22) PCT Filed: Aug. 3, 2012

(86) PCT No.: PCT/EP2012/065269
§ 371 (c)(1),
(2), (4) Date: May 2, 2014

(87) PCT Pub. No.: WO2013/017693
PCT Pub. Date: Feb. 7, 2013

(65) Prior Publication Data
US 2014/0168855 A1  Jun. 19, 2014

(30) Foreign Application Priority Data
Aug. 4, 2011 (FR) ...................................... 11 57159

(51) Int. Cl.
| | |
|---|---|
| *H01G 9/035* | (2006.01) |
| *H01G 11/58* | (2013.01) |
| *C07F 9/54* | (2006.01) |
| *B01J 31/02* | (2006.01) |
| *H01G 9/022* | (2006.01) |
| *H01G 9/00* | (2006.01) |

(52) U.S. Cl.
CPC ............. *H01G 11/58* (2013.01); *B01J 31/0288* (2013.01); *C07F 9/5407* (2013.01); *H01G 9/035* (2013.01); *H01G 9/038* (2013.01); *H01G 2009/0007* (2013.01); *H01G 2009/0025* (2013.01); *H01M 2300/0045* (2013.01); *Y02E 60/13* (2013.01)

(58) Field of Classification Search
CPC .............. H01G 2009/0007; H01G 2009/0025; H01G 9/0035; H01G 9/038; H01M 2300/0045
See application file for complete search history.

(56) References Cited

U.S. PATENT DOCUMENTS

| | | | | |
|---|---|---|---|---|
| 4,189,761 A | * | 2/1980 | Finkelstein | ............ H01G 9/022 252/62.2 |
| 4,478,694 A | * | 10/1984 | Weinberg | ................ C25B 3/105 205/450 |
| 4,584,408 A | * | 4/1986 | Wang | ...................... C07C 41/16 568/48 |
| 4,774,011 A | * | 9/1988 | Mori | ...................... H01G 9/022 252/62.2 |
| 4,889,779 A | | 12/1989 | Connolly et al. | |
| 6,690,573 B2 | * | 2/2004 | Honda | ................... H01G 9/022 361/509 |
| 7,072,173 B2 | * | 7/2006 | Takeda | ................... H01G 9/035 29/25.03 |
| 7,227,738 B2 | * | 6/2007 | Takeda | ................... H01G 9/028 252/62.2 |
| 2004/0141281 A1 | | 7/2004 | Takaoka et al. | |
| 2007/0022541 A1 | | 2/2007 | Taeger et al. | |

FOREIGN PATENT DOCUMENTS

| | | | |
|---|---|---|---|
| EP | 0 246 825 A2 | | 11/1987 |
| EP | 246825 | * | 11/1987 |
| EP | 2174969 | * | 4/2010 |
| WO | 2010 142437 | | 12/2010 |
| WO | WO 2012/031025 | * | 3/2012 |

OTHER PUBLICATIONS

International Preliminary Report on Patentability issued Apr. 10, 2014 in PCT/EP2012/065269 (submitting English language translation only).
Neouze M. et al., "Versatile heat resistant solid electrolytes with performances of liquid electrolytes" Progress in Solid State Chemistry. vol. 33, No. 2-4, pp. 217-222, Jan. 1, 2005 XP 005428554.
International Search Report Issued Feb. 20, 2013 in PCT/EP12/065269 Filed Aug. 3, 2012.
French Preliminary Search Report issued May 10, 2012 in Patent Application No. FR 1157159 (with English translation of categories of cited documents).

* cited by examiner

*Primary Examiner* — Carol M Koslow
(74) *Attorney, Agent, or Firm* — Oblon, McClelland, Maier & Neustadt, L.L.P.

(57) ABSTRACT

The present invention relates to ionic liquids comprising, as cation, a specific phosphonium cation, as anion, a formate anion, which can be used, alone or as a mixture, to constitute electrolytes for energy storage devices.

13 Claims, 2 Drawing Sheets

IONIC LIQUIDS THAT CAN BE USED AS PART OF THE ELECTROLYTE COMPOSITION FOR ENERGY STORAGE DEVICES

TECHNICAL FIELD

The present invention relates to novel ionic liquids resulting from the original association between a specific cation and a specific anion.

These ionic liquids have excellent properties in terms of conductivity, viscosity, electroactivity domain and thermal stability.

Thus, it is quite natural that these ionic liquids can find application as electrolytes in energy storage devices, such as supercapacitors.

STATE OF THE PRIOR ART

Three major types of energy storage device enabling electrical energy to be stored reversibly exist: conventional dielectric capacitors, accumulators or secondary electrochemical generators and supercapacitors.

Supercapacitors have quite particular interest not just for the on-board energy field but also for the portable energy field.

From an operating viewpoint, supercapacitors function on the principle of the "Electrochemical double layer capacitor" (also known by the abbreviation EDLC), i.e. in other words on the principle of energy storage by distribution of ions from an electrolyte in the vicinity of the surface of two porous electrodes impregnated with electrolyte, separated by an insulating and porous membrane assuring ionic conduction.

Thus, a cell based on a supercapacitor may be summarised by the following elements:
  a positive electrode;
  a positive electrode/electrolyte forming a double electrical layer interface;
  an insulating and porous membrane impregnated by said electrolyte;
  a negative electrode; and
  a negative electrode/electrolyte forming a double electrical layer interface.

Due to the existence of these two interfaces each forming an electrochemical double layer, a supercapacitor may be considered schematically as the association in series of two capacitors, one with the positive electrode and the other with the negative electrode, said two capacitors being created by application of a current to the terminals of the supercapacitor, which creates a charge zone at the two electrode-electrolyte interfaces, the energy being thereby stored in an electrostatic and not electrochemical manner.

Three major types of supercapacitors exist:
  carbon based supercapacitors, which conventionally associate two electrodes based on activated carbon, also known as "electrochemical double layer supercapacitors" and are also very often qualified as symmetrical systems, due to the fact that the positive and negative electrodes are identical;
  metal oxide based supercapacitors, which operate on the principle of energy storage by means of a protonation reaction at the surface of noble metal oxide (for example, $RuO_2$ and $IrO_2$) electrodes, this type of supercapacitor remaining earmarked for high added value markets, on account of the costs induced by the use of noble metals;
  supercapacitors, which associate a battery electrode with a supercapacitor electrode, which means these supercapacitors are called "hybrid systems" or instead "asymmetric hybrid systems", due to the fact that they comprise two different electrodes.

It is known that the energy stored and the power delivered by a supercapacitor are a function of the square of the applicable rated voltage, which signifies, in other words, that the performances of a supercapacitor may be considerably improved by playing on the increase of the rated voltage applicable at the terminals of the supercapacitor.

Thus, the maximum potential difference at the terminals of the supercapacitor is conditioned by the nature of the electrolyte and its ability to remain stable in a given electrochemical window. Among other things, it also proves to be necessary that an electrolyte, while being stable over a wide electrochemical window, has the following characteristics:
  a good ionic conductivity;
  a high temperature range;
  a relatively low viscosity so as to enable good mobility of the ions.

At present, three types of electrolytes are used in supercapacitors:
  aqueous electrolytes, consisting of one or more salts dissolved in water;
  organic electrolytes, consisting of one or more salts dissolved in an organic solvent;
  ionic liquids, consisting of a salt that is liquid at ambient temperature.

Concerning aqueous electrolytes, whether they are acid (for example, a sulphuric acid solution) or basic (for example, a potassium hydroxide solution), the applicable rated voltage domain, for water decomposition reasons, is limited to around 1 V, which, to reach conventional voltages (for example, 12 V), require complex layouts of several supercapacitor units to be made. In addition, the accessible temperature range is limited on account of the low solubility of certain salts in aqueous medium, which does not allow these electrolytes to be used at temperatures below −20° C.

Concerning organic electrolytes, they have a wider electrochemical stability window than aqueous electrolytes. An organic solvent commonly used as part of the composition of these electrolytes is acetonitrile. This solvent is not very viscous, dissolves salts very well and is highly dissociating.

In addition:
  it is very stable, both in oxidising and in reducing conditions;
  it has a dipolar moment, which enables the solvation of ions; and
  it has both a high donor number and a high acceptor number, which means that it can behave both as a Lewis acid and as a Lewis base.

However, these electrolytes are not very profitable because they are expensive and the use of certain organic solvents that have a high vapour pressure poses a serious environmental problem, due to the fact that they are difficult to recycle and can evaporate in the surrounding atmosphere during their use.

Concerning ionic liquids, they ideally do not have a measurable vapour pressure and have a high thermal stability, which means that the environmental and safety problems encountered with organic solvents (whether in terms of volatility, evaporation and risks of flammability or explosion) are eliminated with them.

Nevertheless, ionic liquids can have high viscosity and thus low ionic conductivities, which leads to high resistances at ambient temperature.

Thus, whether for aqueous electrolytes, organic electrolytes or ionic liquids, drawbacks inherent in the nature of these electrolytes always appear and there does not exist, at the present time, electrolytes combining at one and the same time advantageous properties in terms of electrochemical stability, ionic conductivity, stability at temperature and viscosity.

The authors thus set themselves the aim of proposing a composition meeting these specificities.

DESCRIPTION OF THE INVENTION

Thus, the authors of the present invention have developed novel ionic liquids having at one and the same time:
  low viscosity, which can be of the order of 3-4 mPa·s;
  high electrochemical stability (with a potential differential that can reach 4 V);
  high thermal stability, for example, between −50° C. and +150° C.;
  high ionic conductivity, for example, which can be greater than 20 mS/cm.

These ionic liquids consist of the innovative association between a phosphonium cation and a formate anion.

It is pointed out that ionic liquid is taken to mean salts existing in the liquid state, said ionic liquids being able to be represented by the following generic formula:

$$A^+X^-$$

in which:
*$A^+$ represents a cation, which is, in this case, a phosphonium cation; and
*$X^-$ represents an anion, generally, which is, in this case, a formate anion.

The phosphonium cation is a cation comprising a positively charged phosphorous atom bonded, by covalence, to four groups and/or chemical elements, identical or different.

This cation can satisfy, advantageously, the following generic formula:

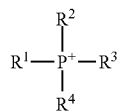

in which $R^1$, $R^2$, $R^3$ and $R^4$ represent, independently of each other, a hydrogen atom, an alkyl group comprising from 1 to 12 carbon atoms, considering that one at least of the $R^1$ to $R^4$ groups represents an alkyl group as defined above.

It is pointed out that alkyl group is conventionally taken to mean, in the foregoing and hereafter, a linear or branched alkyl group of formula $-C_nH_{2n+1}$, n corresponding to the number of carbon atoms, which is, in our case, a number of carbon atoms ranging from 1 to 12.

Advantageously, $R^1$, $R^2$ and $R^3$ may represent an identical alkyl group, such as a tert-butyl group, and $R^4$ represents a hydrogen atom, in which case the cation may be represented by the following formula:

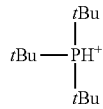

tBu being the abbreviation designating a tert-butyl group, this cation being commonly designated as tri(tert-butyl)phosphonium.

The formate anion (which could also be called methanoate anion) may be represented by the following formula:

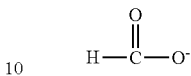

These ionic liquids, which may be used as electrolytes, may be prepared by a simple acidic-basic reaction according to the Brønsted mechanism.

To the ionic liquids may be added water, an organic solvent and/or organic acids.

Thus, the invention also relates to a composition comprising, apart from an ionic liquid as defined above, one or more additives selected from water, an organic solvent, an organic acid and mixtures thereof.

As organic solvent, it may be an aprotic polar solvent, which may be selected, in particular, from nitrile solvents (in other words solvents comprising at least one —CN group), carbonate solvents and lactone solvents (in other words solvents comprising at least one cyclic ester group).

When the solvent is a nitrile solvent, it can be acetonitrile of formula $CH_3-CN$.

Acetonitrile is particularly advantageous and for the following reasons:
  it is not very viscous (its viscosity being of the order of 0.32 mPa·s);
  it dissolves salts very well, because it is highly dissociating, which makes electrolytes comprising acetonitrile cold conductors;
  it is stable from an electrochemical viewpoint, both in oxidising and in reducing conditions;
  it has a dipolar moment, which enables the solvation of ions;
  it has a high Guttman donor number (of the order of 14) and also a high Guttman acceptor number (of the order of 19), which means that it can behave both as an electron acceptor and as an electron donor.

When the solvent is a carbonate solvent, it may be propylene carbonate, ethylene carbonate, dimethyl carbonate, ethyl methyl carbonate (or "EMC").

When the solvent is a lactone solvent, it may be γ-butyrolactone, β-butyrolactone, γ-valerolactone, δ-valerolactone and γ-caprolactone.

As organic acid, it may be a carboxylic acid, for example comprising from 1 to 12 carbon atoms, such as formic acid.

The compositions of the invention may be prepared by simple preparation methods within the scope of those skilled in the art.

Thus, the compositions may be prepared according to the following sequence of steps:
  a step of weighing each of the constituent ingredients of the composition;
  a step of formation of the composition by mixing said ingredients.

The compositions of the invention form, on account of the presence of an ionic liquid, an electrolytic mixture, which means that they are particularly appropriate to be used as electrolytes, which is also the case of ionic liquids as such, in an energy storage device, preferably, of the supercapacitor type.

The invention thus also relates to an energy storage device, for example, of supercapacitor type, as illustrated according to a particular embodiment in the single appended figure, comprising at least one cell 1 comprising a positive electrode 3 and a negative electrode 5 separated from each other by a separator 7 comprising, as electrolyte, an ionic liquid or a composition according to the invention.

The positive electrode and the negative electrode may be based on activated carbon, in which case supercapacitors comprising this type of electrode may be qualified as symmetrical systems.

The positive electrode and the negative electrode may also be based on metal oxide(s).

The ionic liquid or the composition according to the invention forms at the level of each electrode-separator interface an electrochemical double layer.

The invention will now be described with reference to the examples provided below given by way of illustration and non-limiting.

DETAILED DESCRIPTION OF PARTICULAR EMBODIMENTS

EXAMPLE 1

Figure 1:
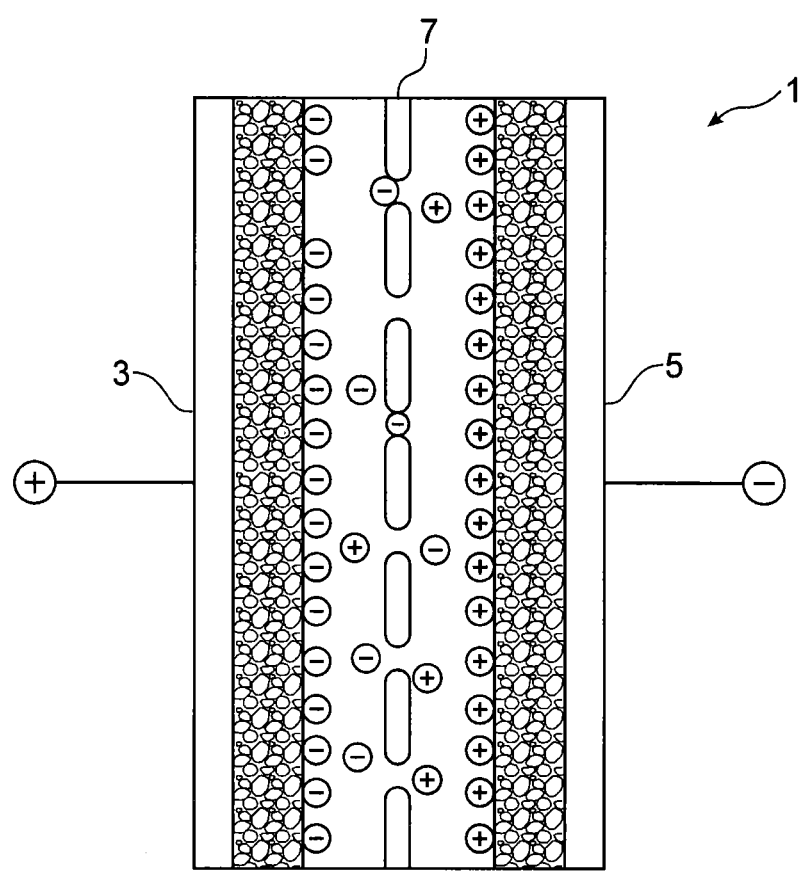
FIG. 1 represents a supercapacitor cell according to the invention.

This example illustrates the preparation of the protic ionic liquid resulting from the association of a tri(tert-butyl)phosphonium cation and a formate anion, formed by proton transfer between a Brønsted acid (here, formic acid) and a Brønsted base (here, tri(tert-butyl)phosphine).

To do so, 0.402 mole of formic acid (98%) (m=18.91 g; V=15.5 cm$^3$) are mixed with 0.462 moles of tri(tert-butyl) phosphine (m=81.47 g; V=100.5 cm$^3$) at ambient temperature under stirring in ethyl acetate (50 mL).

The resulting mixture is stirred for 48 hours.

At the end of these 48 hours, the mixture is evaporated under vacuum at 80° C., so as to eliminate excess tri(tert-butyl)phosphine and formic acid. The ionic liquid thereby obtained is dried under vacuum. After drying, Karl-Fisher analysis indicates the presence of 1.6% of residual water. This water resists elimination, because it forms a solvate with the ionic liquid.

The ionic liquid obtained is thus 98.4% pure. It is transparent and has no odour.

EXAMPLE 2

In this example, the ionic liquid prepared in example 1 is mixed with formic acid (according to a 1/10 molar ratio, which signifies that, for 100 g of mixture, there is 35 g of ionic liquid and 65 g of formic acid). The resulting composition is hereafter designated [TrBuPh][HCOO]/10HCOOH.

The conductivity was measured as a function of temperature.

It indicates that the conductivity increases substantially as a function of temperature, amounting to 35 mS·cm$^{-1}$ at 25° C. and to 47.9 mS·cm$^{-1}$ at 50° C. These conductivity values are much higher than those conventionally encountered for ionic liquids (which are generally below 15 mS·cm$^{-1}$).

The conductivity of this composition was also measured, as a function of mass content.

To do so, different weight proportions of water were added and for each of the resulting compositions the conductivity of the composition was measured at 25° C.

It was noted that the conductivity remains substantially constant for weight proportions of water ranging from 0 at 0.8.

EXAMPLE 3

In this example, the ionic liquid prepared in example 1 is mixed with formic acid (according to a 1/10 molar ratio, which signifies that, for 100 g of mixture, there is 35 g of ionic liquid and 65 g of formic acid). The resulting composition is designated hereafter [TrBuPh][HCOO]/10HCOOH.

The viscosity was measured as a function of temperature.

It turns out that this reaches 3.7 cP at 25° C. and 2.5 cP at 50° C., these values being lower than those of ionic liquids presently studied in the literature (the values for these liquids lying around 80 cP at 20° C.)

EXAMPLE 4

In this example, the ionic liquid prepared in example 1 is subjected to a thermal analysis performed by differential scanning calorimetry (also called "DSC").

To do so, a 11 mg sample of the ionic liquid is subjected, under nitrogen atmosphere, to two cycles comprising a rise in temperature from 25° C. to 350° C. at a rate of 10° C./min and a cooling from 350° C. to 25° C. also at a rate of 10° C./min.

It appears from this analysis that the ionic liquid is stable between 25° C. and 350° C.

EXAMPLE 5

In this example, the ionic liquid prepared in example 1 is mixed with formic acid (according to a 1/10 molar ratio, which signifies that, for 100 g of mixture, there is 35 g of ionic liquid and 65 g of formic acid). The resulting composition is hereafter designated [TrBuPh][HCOO]/10HCOOH.

Figure 2:
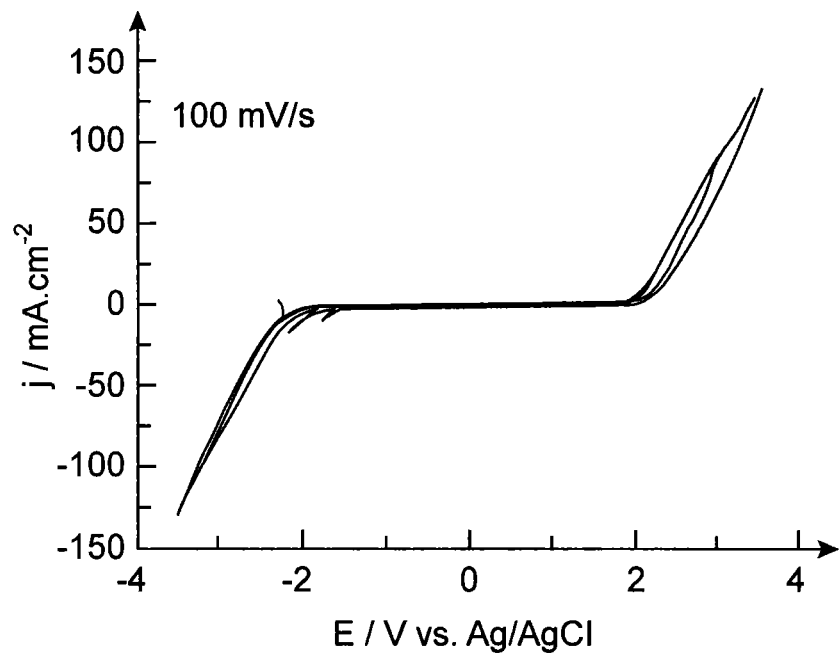
FIGS. 2 and 3 represent cyclic voltamperometry graphs representing the evolution of the current density j (in mA·cm$^{-2}$) as a function of the potential E (in V with respect to a reference Ag/AgCl electrode) respectively for a scanning speed of 100 mV/s and 10 mV/s for compositions according to example 5 below.
Figure 3:
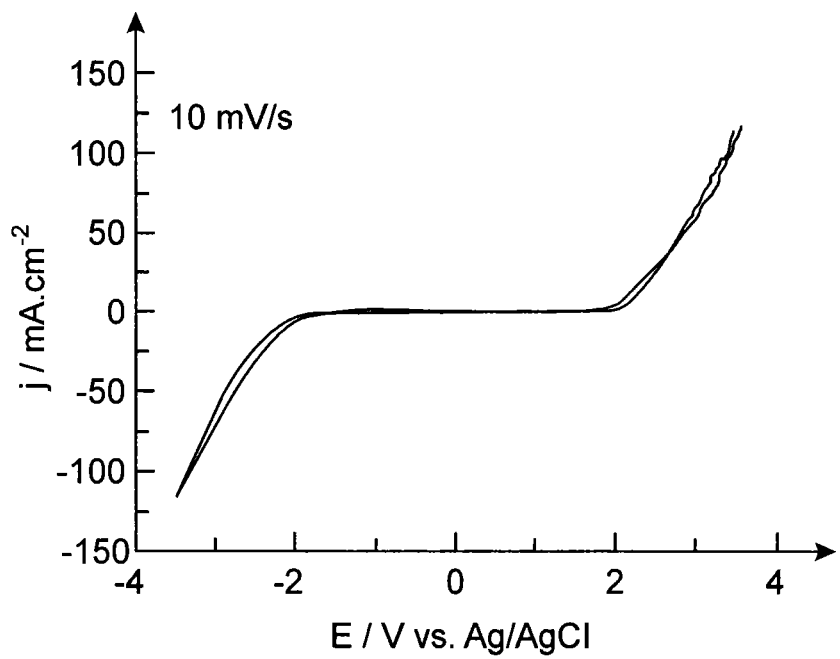

The resulting composition is subjected to cyclic voltamperometry tests by the three electrodes method at ambient temperature and at different scanning speeds (a series of tests at 100 mV/s for FIG. 2 and a series of tests at 10 mV/s for FIG. 3).

As may be seen in FIGS. 2 and 3 representing the current density j (in mA·cm$^{-2}$) as a function of the potential E (in V), it turns out that the resulting composition has an electrochemical stability over a 4 V window, and more precisely from −2V to +2V expressed with respect to an Ag/AgCl reference electrode.

EXAMPLE 6

In this example, three compositions have been developed:
a first composition resulting from mixing the ionic liquid prepared in example 1 with formic acid (according to a 1/10 molar ratio, which signifies that, for 100 g of mixture, there is 35 g of ionic liquid and 65 g of formic acid). The resulting composition is hereafter designated [TrBuPh][HCOO]/10HCOOH;
a second composition resulting from mixing the aforementioned first composition with acetonitrile (for 100 g of mixture, 50 g of the first composition and 50 g of acetonitrile);

a third composition resulting from mixing the aforementioned first composition with water (for 100 g of mixture, 50 g of the first composition and 50 g of water).

These three compositions are subjected to cyclic voltamperometry tests on activated carbon in standard scanning speed conditions (namely 20 mV/s).

The following respective capacity values are deduced therefrom:

C=150 F/g for the first composition;
C=200 F/g for the second composition; and
C=160 F/g for the third composition.

The Maximum theoretical capacities are attained in all cases.

The same tests were carried out with an aqueous electrolyte comprising water and $K_2SO_4$ (1 mol·$L^{-1}$) and an organic electrolyte (a mixture of ethyl carbonate and dimethyl carbonate and LiTFSI (1 mol·$L^{-1}$) (TFSI signifying (trifluoromethanesulphonyl)imide).

They indicate that the use of compositions according to the invention makes it possible to improve the capacitive behaviour of the cells in which they are included.

EXAMPLE 7

In this example, three compositions have been developed:
a first composition resulting from mixing the ionic liquid prepared in example 1 with formic acid (according to a 1/10 molar ratio, which signifies that, for 100 g of mixture, there is 35 g of ionic liquid and 65 g of formic acid). The resulting composition is hereafter designated [TrBuPh][HCOO]/10HCOOH;
a second composition resulting from mixing the aforementioned first composition with acetonitrile (for 100 g of mixture, 50 g of the first composition and 50 g of acetonitrile);
a third composition resulting from mixing the aforementioned first composition with water (for 100 g of mixture; 50 g of the first composition and 50 g of water).

These three compositions are subjected to cyclic voltamperometry tests on activated carbon in high scanning speed conditions (namely 100 mV/s).

The following respective capacity values are deduced therefrom:

C=180 F/g for the first composition;
C=180 F/g for the second composition; and
C=268 F/g for the third composition.

It may be concluded from this that the use of compositions according to the invention allows high applied current densities (for example, from 40 A/g to 60 A/g). They have all the characteristics necessary for applications requiring both high energy densities and power.

EXAMPLE 8

In this example, the ionic liquid prepared in example 1 is mixed with formic acid (according to a 1/10 molar ratio, which signifies that, for 100 g of mixture, there is 35 g of ionic liquid and 65 g of formic acid). The resulting composition is hereafter designated [TrBuPh][HCOO]/10HCOOH.

The resulting composition is subjected to cyclic voltamperometry tests on activated carbon electrode with a scanning speed of 5 mV/s at different temperatures (25° C., 80° C. and −40° C.).

The following respective capacity values are deduced therefrom:

C=150 F/g for a temperature of 25° C.;
C=155 F/g for a temperature of 80° C.; and
C=150 F/g for a temperature of −40° C.

Considering the substantially equivalent capacity values, it follows that the composition according to the invention has a stable capacitive behaviour over a wide range of temperatures (such as between −40 and 80° C.)

The invention claimed is:

1. An ionic liquid, comprising:
as cation, a phosphonium cation; and
as anion, a formate anion,
wherein:
the phosphonium cation satisfies the following generic formula:

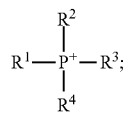

and
$R^1$, $R^2$ and $R^3$ represent an identical alkyl group and $R^4$ represents a hydrogen atom, wherein said alkyl group comprises from 1 to 12 carbon atoms.

2. The ionic liquid according to claim 1, wherein $R^1$, $R^2$ and $R^3$ represent a tert-butyl group.

3. A composition, comprising:
the ionic liquid of claim 1; and
at least one additive selected from the group consisting of water, an organic solvent, an organic acid and a mixture thereof.

4. The composition according to claim 3, comprising an aprotic polar solvent as the organic solvent.

5. The composition according to claim 3, comprising the organic solvent which is selected from the group consisting of a nitrile solvent, a carbonate solvent and a lactone solvent.

6. The composition of claim 3, comprising acetonitrile as the organic solvent.

7. The composition of claim 3, comprising a carboxylic acid as the organic acid.

8. The composition according to claim 7, wherein the carboxylic acid is formic acid.

9. The composition of claim 3, which is an electrolyte.

10. An energy storage device, comprising at least one cell comprising a positive electrode and a negative electrode separated from each other by a separator comprising, as electrolyte, the ionic liquid of claim 1.

11. The energy storage device according to claim 10, which is a supercapacitor.

12. An energy storage device, comprising at least one cell comprising a positive electrode and a negative electrode separated from each other by a separator comprising, as electrolyte, the composition of claim 3.

13. The energy storage device according to claim 12, which is a supercapacitor.

* * * * *